United States Patent [19]
Ezio

[11] Patent Number: 5,795,371
[45] Date of Patent: Aug. 18, 1998

[54] DEVICE AND METHOD FOR THE STERILIZATION OF COMPRESSED AIR FOR MEDICAL USE

[76] Inventor: Bartocci Ezio, Via L. Da Vinci 32, Piacenza, Italy

[21] Appl. No.: 899,379

[22] Filed: Jul. 23, 1997

[30] Foreign Application Priority Data

Jul. 29, 1996 [IT] Italy ................... PC96A0018

[51] Int. Cl.$^6$ ................... B01D 50/00
[52] U.S. Cl. ................... 96/175; 55/525; 55/526; 422/307
[58] Field of Search ................... 95/283; 55/525, 55/526; 422/307; 417/290, 313; 137/340; 96/175

[56] References Cited

U.S. PATENT DOCUMENTS

| | | | |
|---|---|---|---|
| 3,734,122 | 5/1973 | Cousins | 137/340 |
| 3,966,407 | 6/1976 | Buckerberg et al. | 422/307 |
| 5,222,871 | 6/1993 | Meyer et al. | 417/313 |
| 5,441,710 | 8/1995 | Marois | 55/525 |
| 5,526,841 | 6/1996 | Detsch et al. | 137/15 |
| 5,551,845 | 9/1996 | Milam | 417/290 |

*Primary Examiner*—Jay H. Woo
*Assistant Examiner*—Minh-Chau T. Pham
*Attorney, Agent, or Firm*—Notaro & Michalos P.C.

[57] ABSTRACT

An apparatus and method for sterilizing air for medical uses applied to air compressors used in dentists' apparatuses. According to the invention, we use the heat of the air coming out from the air outlet provided on the head of the compressor, to reduce the bacterial charge of a filtering cartridge fitted on the conduits that feed the air to the devices. A body contains a sterilizing cartridge and a pipe coil or a conduit through which the air coming out of the head of the compressor passes, so that it is possible to use this heat for heating the cartridge thus reducing the bacterial charge of the same every time the compressor is turned on, without the need of disassembling parts or components.

8 Claims, 2 Drawing Sheets

5,795,371

DEVICE AND METHOD FOR THE STERILIZATION OF COMPRESSED AIR FOR MEDICAL USE

FIELD AND BACKGROUND OF THE INVENTION

The present invention relates to an apparatus and the relevant method for sterilizing air for medical use, and in particular relates to a device that is applied to the air compressors used in the dentists' apparatuses. According to the invention, we use the heat of the air coming out from the air outlet provided on the head of the compressor, to reduce the bacterial charge of a filtering cartridge fitted on the conduits that feed the air to the devices.

In particular the device comprises a body containing said sterilizing cartridge and enclosing a pipe coil or a conduit through which the air coming out of the head of the compressor passes, so that it is possible to use this heat for heating the cartridge thus reducing the bacterial charge of the same every time the compressor is turned on, without the need of disassembling parts or components.

There are several cases, in particular in the field of dental care, in which air treated against bacteria is needed.

For instance, in the case of the dentists' apparatuses air jets are used for cleaning operations, for driving the drills, for the cooling of the tools, etc. Since these air jets often get in contact with wounds, we need to be sure that the air is sterile.

For this purpose the air, taken from a tank, is driven to the apparatuses passing through a sterilizing filter.

In the known devices these filters are placed along an air feeding pipe, and are housed in boxes that can be disassembled or opened, so as to allow the removal of the filter for periodical sterilization.

These operations, even if not particularly difficult, need time and diligence of the operator, who disassembles the filter, sterilizes it in an autoclave and assembles it again.

This is the reason why one often forget or fail doing it.

SUMMARY OF THE INVENTION

The present invention relates to this field and proposes a device for air sterilization comprising a body which contains a filtering cartridge and that has a pipe coil or conduit connected at one side to the air outlet on the head of a compressor and at the other side to a tank for the compressed air. In this way it is possible the make use of the heat of the air leaving the compressor to reduce the bacterial charge of the cartridge every time the device is turned on.

BRIEF DESCRIPTION OF THE DRAWINGS

The present invention will now be described in detail, as an example, with reference to the following figures.

DESCRIPTION OF THE PREFERRED EMBODIMENTS

Figure 2:
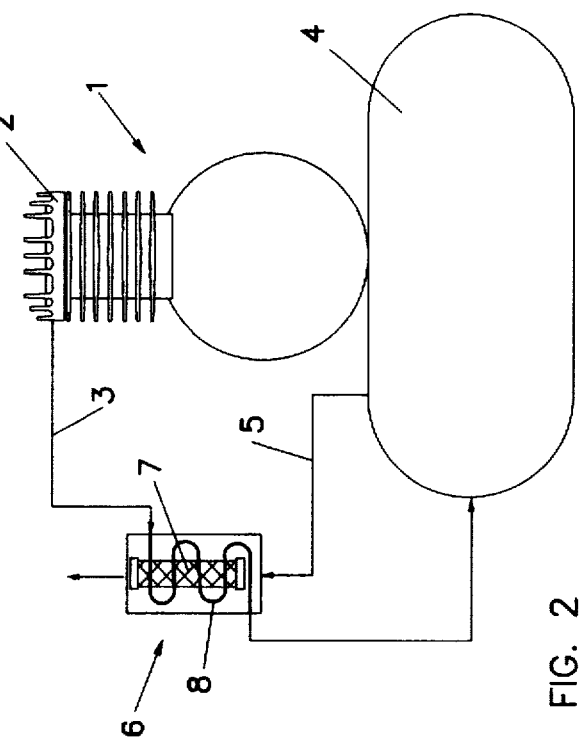
FIG. 2 shows schematically the lay-out of a device for the production of sterilized compressed air.

Reference is made to FIG. 2, that shows a scheme of a device for the production of sterilized compressed air.

Number 1 shows a compressor in its whole, wherein the head 2 is connected, through a conduit 3, to a storage tank 4.

Number 5 indicates the outlet conduit of the tank, which passes through a sterilization device indicated as a whole with number 6.

This conduit is connected to the tools of a dentists' apparatus.

According to the invention, this sterilizing device comprises a sterilizing cartridge 7 housed in the body 6 and a conduit or a pipe coil 8, which is part of the air supply circuit 3 from the head to the tank.

This pipe coil is fitted all around the cartridge, so that the compressed air coming out from the head 2, may disperse its heat to the cartridge itself, which is so thermally treated.

Figure 1:
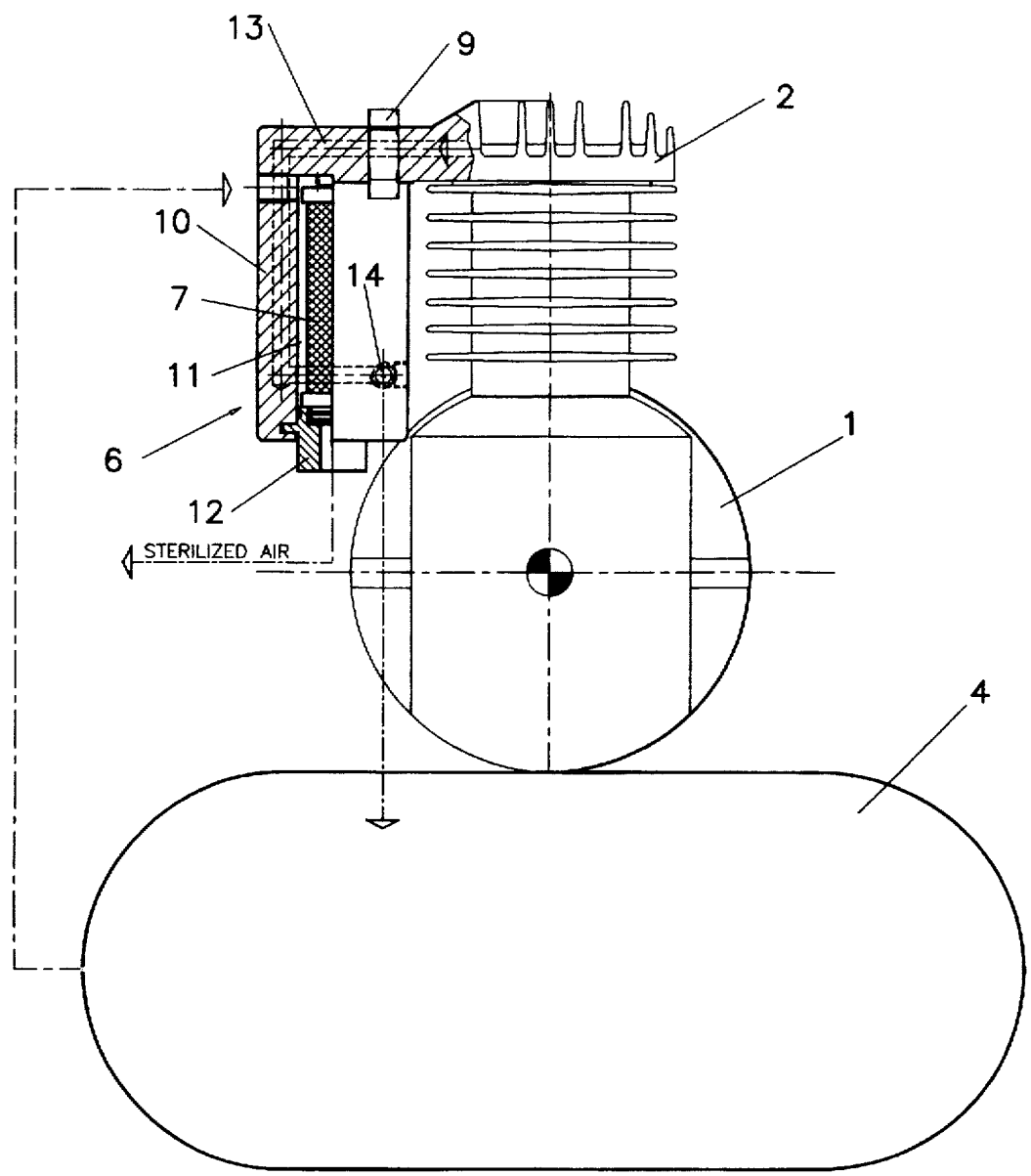
FIG. 1 schematically shows a device according to the invention applied to a compressor.

FIG. 1 shows in details the device according to the invention.

Number 1 indicates the body of the compressor, while number 2 indicates the head of a cylinder in which the air is compressed.

The air comes out through a connection 9.

A sterilization device 6—comprising a body 10 provided with a seat 11 housing the cartridge 7—is applied to the compressor.

A connection 12 is both used to keep the cartridge in its seat and to feed it with the compressed air coming from the tank.

The body 10 is also provided with a conduit, preferable pipe-coil-shaped, indicated as n. 3 in the figure, that connects the attach 9 on the outlet of the head 2 with a conduit 14 directed to the storage tank.

When the compressor is turned on, the air comes out from the head 2, through the connection 9, at a high temperature, usually from 100° to 130° C.

The air then passes through the pipe coil 13 where it cedes its heat by convection to the body 10.

When the air comes out from the pipe coil, it is directed to the storage tank along the conduit 14 and, when it is used, it comes out from the tank to go to the tools passing through the sterilizing cartridge.

The heat that has been transferred to the body 10 by the air leaving the head 2, heats also the cartridge 7, that is then treated every time the compressor is used, thus avoiding the need to remove it from its seat.

Figure 5:
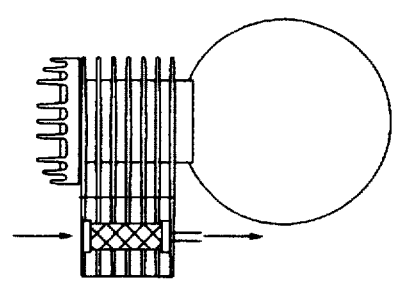
FIG. 3–5 schematically show different embodiments of the device according to the invention.
Figure 3:
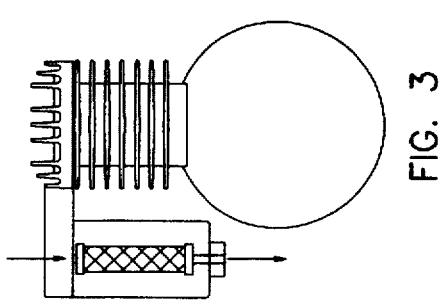
Figure 4:
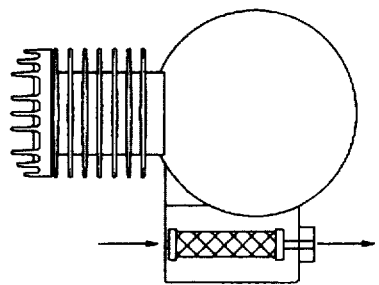

The device according to the invention could then be made in different embodiments, some of which are schematically shown in FIG. 3–5.

The seat of the cartridge could be obtained in a body fitted to the head of the cylinder as shown in FIG. 3, or could be obtained directly from the block of the compressor as shown in FIG. 4. It could also be obtained directly from the cooling wings of the head of the cylinder, in order to use the heat produced by the air compression to raise the temperature of the cartridge enough to ensure the sterilization.

I claim:

1. A compressed air sterilization device for medical use, comprising: means for compressing air which produces heat sufficient to sterilize a filtering cartridge; a filtering cartridge for passing air from the means for compressing air; and means provided which use the heat produced during the air compression to heat the filtering cartridge to a temperature high enough to insure a thermal treatment of the air passing through the filtering cartridge.

2. Compressed air sterilization device according to claim 1, comprising a compressor for obtaining compressed air, a storage tank for said compressed air, a body that contains a filtering cartridge, said filtering cartridge being connected with to the air outlet of said tank to eliminate the bacterial charge of the air leaving said tank, the device further comprising means to direct the hot air coming out from the compressor to said body containing said cartridge, in order to heat this cartridge at a temperature high enough to avoid the proliferation of the bacterial charge.

3. Device according to claim 2, wherein said means that direct the hot air from the compressor to the filtering cartridge, comprise a conduit, fitted inside said body around the seat of said cartridge, said conduit connecting the outlet of the compressor with the inlet of said storage tank.

4. Device according to claim 2, wherein said filtering cartridge is fitted in a seat provided in the wings of the compressor cylinder.

5. Device according to claim 2, wherein the seat of said cartridges is fitted directly into the body of the compressor.

6. Method for the sterilization of compressed air for medical use, comprising: producing heat by compressing the air and using the heat produced during the air compression to heat a filtering cartridge to a temperature high enough to avoid proliferation of a bacterial charge in the cartridge without any other heat source; and passing the compressed air through the filtering cartridge.

7. Device according to claim 1 wherein the means which use the heat is free of any heating source other than heat produced by compressing air by the means for compressing air.

8. Device according to claim 2 wherein the filtering cartridge is heated only by heat from the hot air and by no other heating source.

* * * * *